US00PP34505P2

(12) United States Plant Patent
Schoone

(10) Patent No.: US PP34,505 P2
(45) Date of Patent: Aug. 16, 2022

(54) ***PHALAENOPSIS* PLANT NAMED 'MOTHERS FINEST'**

(50) Latin Name: *Phalaenopsis hybrida*
Varietal Denomination: 'Mothers Finest'

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/666,222

(22) Filed: Feb. 7, 2022

Related U.S. Application Data

(60) Provisional application No. 63/147,984, filed on Feb. 10, 2021.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Phalaenopsis* plant named 'Mothers Finest', characterized by its upright plant habit; moderately vigorous growth habit; strong flowering stems; strong and moderately elongated leaves; freely flowering habit with typically two inflorescences per plant, each inflorescence with numerous flowers; greenish white-colored flowers with random small to large purplish red-colored spots; and good postproduction longevity.

2 Drawing Sheets

Figure 1:
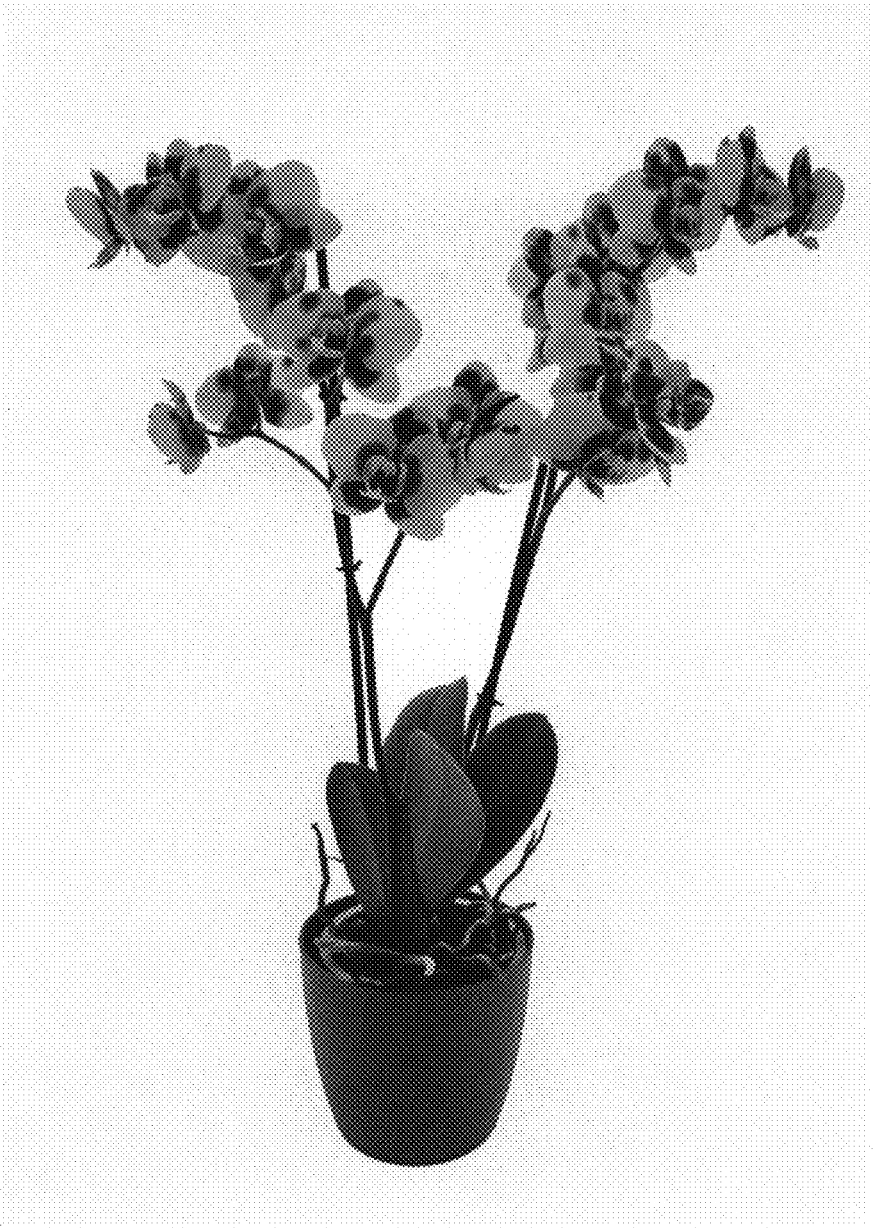

Botanical designation: *Phalaenopsis hybrida.*
Cultivar denomination: 'MOTHERS FINEST'.

STATEMENT REGARDING PRIOR DISCLOSURES BY INVENTOR and APPLICANT/ASSIGNEE

An European Community Plant Breeder's Rights application for the instant plant was filed by the Applicant/Assignee of the instant application, Floricultura B.V. of Heemskerk, The Netherlands on Mar. 18, 2021, application number 2021/0834. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Mothers Finest'.

The new *Phalaenopsis* plant is a product of a planned breeding program conducted by the Inventor in Nantou, Taiwan and Heemskerk, The Netherlands. The objective of the breeding program is to develop new fast-growing and freely flowering *Phalaenopsis* plants with good leaf shape and large flowers with unique and attractive patterns and coloration.

The new *Phalaenopsis* plant originated from a cross-pollination on May 20, 2014 in Nantou, Taiwan of *Phalaenopsis hybrida* 'Diamond Beauty', not patented, as the female, or seed, parent with *Phalaenopsis hybrida* 'Snow Leopard', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in August, 2018.

Asexual reproduction of the new *Phalaenopsis* plant by in vitro meristem propagation in a controlled environment in Assendelft, The Netherlands since August, 2019 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Mothers Finest'. These characteristics in combination distinguish 'Mothers Finest' as a new and distinct *Phalaenopsis* plant:

1. Upright plant habit.
2. Moderately vigorous growth habit.
3. Strong flowering stems.

4. Strong and moderately elongated leaves.
5. Freely flowering habit with typically two inflorescences per plant, each inflorescence with numerous flowers.
6. Greenish white-colored flowers with random small to large purplish red-colored spots.
7. Good postproduction longevity.

Plants of the new *Phalaenopsis* can be compared to plants of the female parent, 'Diamond Beauty'. Plants of the new *Phalaenopsis* differ primarily from plants of 'Diamond Beauty' in flower color as plants of the new *Phalaenopsis* have greenish white-colored flowers with purplish red-colored spots whereas plants of 'Diamond Beauty' have yellow-colored flowers with more numerous spots.

Plants of the new *Phalaenopsis* can be compared to plants of the male parent, 'Snow Leopard'. Plants of the new *Phalaenopsis* differ primarily from plants of 'Snow Leopard' in flower color as plants of the new *Phalaenopsis* have greenish white-colored flowers with purplish red-colored spots whereas plants of 'Snow Leopard' have white-colored flowers with more numerous spots.

Plants of the new *Phalaenopsis* can be compared to plants of *Phalaenopsis hybrida* 'Big Time', not patented. In side-by-side comparisons, plants of the new *Phalaenopsis* differ primarily from plants of 'Big Time' in flower color as plants of the new *Phalaenopsis* have greenish white-colored flowers with purplish red-colored spots whereas plants of 'Big Time' have white-colored flowers with fewer spots.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Mothers Finest' grown in a container.

Figure 2:
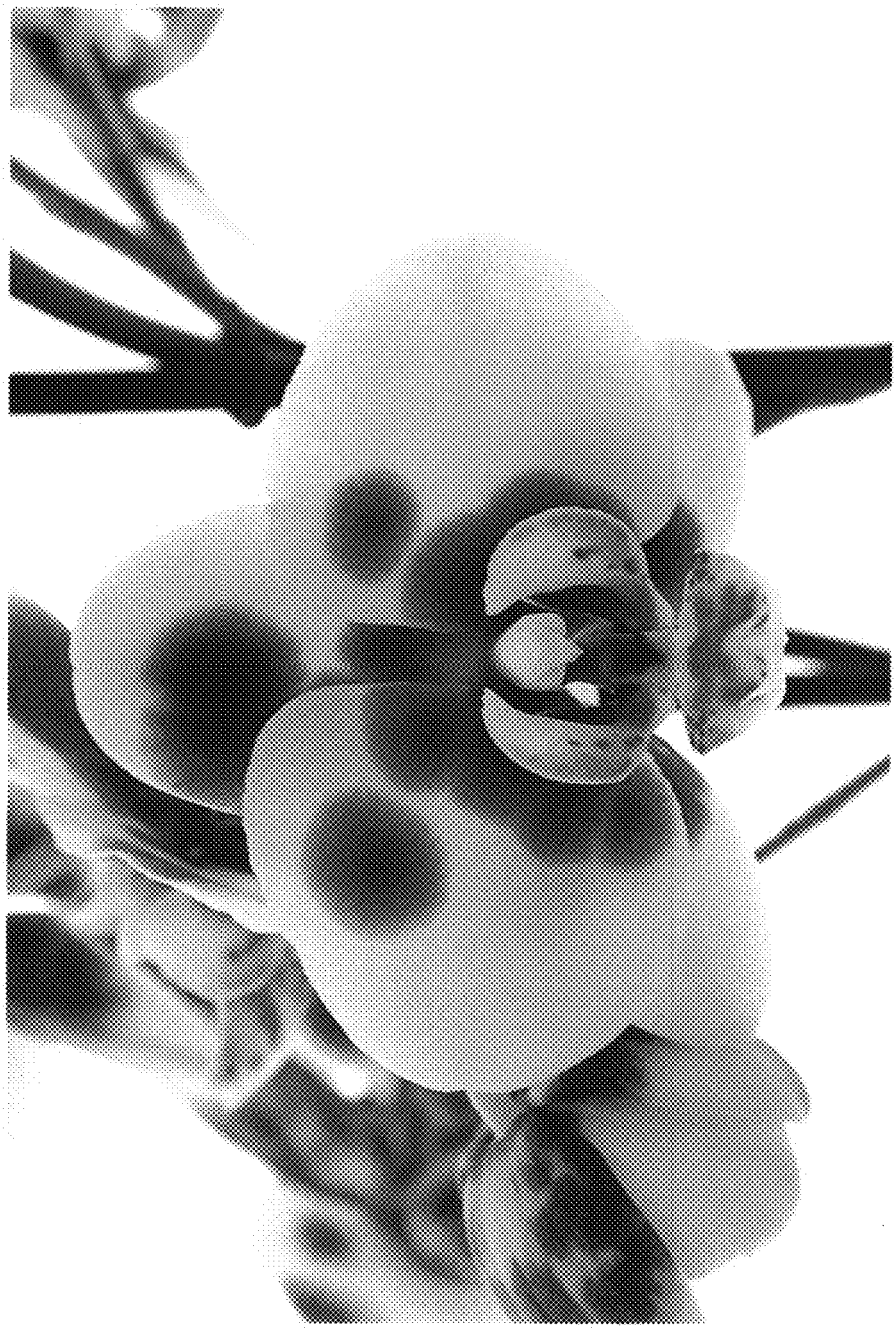

The photograph on the second sheet (FIG. 2) is a close-up view of typical flowers of 'Mothers Finest'.

DETAILED BOTANICAL DESCRIPTION

The aforementioned photographs and following observations and measurements describe plants grown during the late summer and early autumn in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the production of the plants, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Mothers Finest'.

Parentage:

*Female parent.*—*Phalaenopsis hybrida* 'Diamond Beauty', not patented.

*Male parent.*—*Phalaenopsis hybrida* 'Snow Leopard', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically two inflorescences per plant, each inflorescence with numerous flowers; monopodial; moderately vigorous growth habit and moderate growth rate.

*Plant height, substrate level to top of foliar plane.*—About 12.3 cm.

*Plant height, substrate level to top of inflorescences.*—About 40.5 cm.

*Plant diameter or spread.*—About 28.1 cm.

Leaf description:

*Arrangement and quantity.*—Distichous, simple; sessile; about eight leaves per plant.

*Length.*—About 14.7 cm.

*Width.*—About 5.4 cm.

*Aspect.*—Upright to outwardly arching.

*Shape.*—Oblanceolate; slightly carinate.

*Apex.*—Unequal obtuse to unequal broadly acute.

*Base.*—Sheathing. Sheath length: About 1.9 cm. Sheath width: About 1.4 cm. Sheath color: Close to 143C; apical margin, slightly tinged with close to 183A.

*Margin.*—Entire; not undulate.

*Texture and luster, upper and lower surfaces.*—Smooth, glabrous; slightly glossy.

*Venation pattern.*—Camptodromous.

*Color.*—Developing leaves, upper surface: Close to NN137B. Developing leaves, lower surface: Close to 146B heavily mottled with close to N186C. Fully expanded leaves, upper surface: Close to NN137A; venation, close to NN137A. Fully expanded leaves, lower surface: Close to 146A to 146B; venation, close to 143A.

Inflorescence description:

*Appearance and flowering habit.*—Showy zygomorphic flowers arranged on axillary branched racemes; typically two inflorescences per plant; each inflorescence with about twelve flowers; flowers face outwardly on arching inflorescences supported by upright peduncles; flowers with three petals, two lateral petals and one center petal transformed into a labellum and three sepals.

*Fragrance.*—None detected.

*Time to flower.*—Plants begin flowering about six months after planting; plants flower naturally during the winter into the spring.

*Flower longevity.*—Long flowering period, individual flowers maintain good substance for about eight weeks on the plant; flowers not persistent.

*Inflorescence length* (*lowermost flower to inflorescence apex*).—About 24.6 cm.

*Inflorescence width.*—About 20.3 cm.

*Flower buds.*—Height: About 2.4 cm. Diameter: About 1.8 cm by 2 cm. Shape: Broadly ovate. Color: Close to 146B and 150C heavily and irregularly blotched and marbled with close to N79A, N79B, N186C and 187A.

*Flower size.*—About 7.8 cm (vertical) by 7 cm (horizontal).

*Flower depth.*—About 3.4 cm.

*Petals, quantity and arrangement.*—Three, two lateral petals and one center petal transformed into a labellum.

*Lateral petals.*—Length: About 3.7 cm. Width: About 4 cm. Shape: Reniform. Apex: Obtuse to rounded. Margin: Entire. Texture and luster, upper and lower surfaces: Smooth, glabrous, velvety; matte. Color: When opening, upper surface: Close to 145D to lighter than 145D; irregularly spotted with close to N79C and 187B. When opening, lower surface: Close to 145C to 145D; irregularly spotted with close to N77A and N77B. Fully opened, upper surface: Close to 157D to lighter than 157D; irregularly spotted with close to 71A, N79B, N79C and N186D; color does not change with subsequent development. Fully opened, lower surface: Close to lighter than 145D; towards the margins, close to 157D to lighter than 157D; irregularly spotted with close to N77B; color does not change with subsequent development.

*Labella.*—Appearance: Three-parted with two lateral lobes and a central lobe. Length, lateral lobes: About 1.8 cm. Width, lateral lobes: About 1.1 cm. Length, central lobe: About 3.1 cm. Width, central lobe: About 8 mm to 17.5 mm. Shape, lateral lobes: Obovate. Shape, central lobe: Roughly deltoid. Apex, lateral lobes: Obtuse. Apex, central lobe: Broadly retuse with two recurved cirrose tips, about 4 mm in length and about 1.2 mm in width. Margins, lateral and central lobes: Entire. Texture and luster, upper and lower surfaces: Smooth, glabrous, moderately velvety; matte. Callosities: Located at the base of the labellum and attachment point of the lateral petals; about 4 mm in length, about 3 mm in width and about 3.5 mm in height. Color: When opening and fully opened, upper surface: Lateral lobes: Close to NN155D; basal margin, close to 13C; fine dots, close to 181B; at the base, close to 187A. Central lobe: Close to 1B; towards the apex, close to 3C; distally, fine dots, close to 187A and proximally, larger spots, close to 72A; at the base, close to a blend of N79B and 187B; cirrose tips, close to NN155D. Callosities: Close to 14C to 14D; distally, close to 183A to 183B. When opening and fully opened, lower surface: Lateral lobes: Close to N155A; basal margin, close to 11A; fine dots, close to 181B; at the base, close to N77A. Central lobe: Close to 160D; towards the apex, close to NN155D; margins, tinged with sloe to 1A to 1B; distally, fine dots, close to 183A and proximally, larger spots, close to 71A; at the base, close to 197B; cirrose tips, close to NN155D.

*Sepals.*—Quantity and arrangement: Three, one upper dorsal sepal and two lower lateral sepals. Length, dorsal sepal: About 4 cm. Width, dorsal sepal: About 2.8 cm. Length, lateral sepals: About 3.8 cm. Width, lateral sepals: About 2.4 cm. Shape, dorsal sepal: Elliptic to oblong. Shape, lateral sepals: Ovate to elliptic. Apex, dorsal sepal: Obtuse. Apex, lateral sepals: Bluntly acute. Base, dorsal and lateral sepals: Truncate. Margin, dorsal and lateral sepals: Entire. Texture and luster, dorsal and lateral sepals, upper and lower surfaces: Smooth, glabrous, velvety; matte. Color, dorsal sepal: When opening, upper surface: Close to 145D; heavily spotted with close to N79A, N186C and N186D. When opening, lower surface: Close to 145B and 145C; heavily spotted with close to N186C, N186D and 187A. Fully opened, upper surface: Close to 157B to 157C; heavily spotted with close to 71A, N79A, N79B, N186D and 187A. Fully opened, lower surface: Close to 145B; towards the margins, close to 157A; heavily spotted with close to N79B, N79C and N186D. Color, lateral sepals: When opening, upper surface: Close to 145D; proximally, close to N79A, N186C and N186D. When opening, lower surface: Close to 145C; midvein, close to 145A to 145B; proximally, close to N186C, N186D and 187A. Fully opened, upper surface: Slightly lighter than 145D; proximally, close to 71A, N79A, N79B, N186D and 187A. Fully opened, lower surface: Close to a blend of 145C and 145D; midvein, close to 145B; heavily spotted with close to N79B, N79C and N186D.

*Peduncles.*—Length: About 41 cm. Diameter: About 4.5 mm. Strength: Strong. Aspect: Upright to outwardly arching. Texture and luster: Smooth, glabrous; matte. Color: Close to 138A; heavily covered with fine dots and stripes, close to 197A; proximally, close to 200A.

*Pedicels.*—Length: About 3.6 cm. Diameter: About 3 mm. Strength: Moderately strong. Aspect: About 50° from peduncle axis. Texture and luster: Smooth, glabrous; matte. Color: Close to 144B; distally, close to 145D, and proximally, spotted and tinged with close to N77B and 147A.

*Reproductive organs.*—Androecium: Column length: About 1.1 cm. Column width: About 6 mm. Column color: Close to NN155C; proximally, close to N78D. Pollinia quantity: Two. Pollinia diameter (per two pollinia): About 3 mm. Pollinia color: Close to 17B. Gynoecium: Stigma length: About 3 mm. Stigma width: About 5 mm. Stigma shape: Reniform. Stigma color: Close to N155A. Ovary length: About 7 mm. Ovary diameter: About 1 mm. Ovary color: Close to 149C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Mothers Finest' as illustrated and described.

* * * * *